US006860603B2

(12) United States Patent
Hirohara et al.

(10) Patent No.: US 6,860,603 B2
(45) Date of Patent: Mar. 1, 2005

(54) BEST CORRECTED VISUAL ACUITY CHARACTERISTICS MEASURING DEVICE, BEST CORRECTED VISUAL ACUITY CHARACTERISTICS MEASURING METHOD, CONTRAST SENSITIVITY MEASURING DEVICE, CONTRAST SENSITIVITY MEASURING METHOD, AND CONTRAST SENSITIVITY TARGET DISPLAYING DEVICE

(75) Inventors: Yoko Hirohara, Tokyo (JP); Toshifumi Mihashi, Tokyo (JP)

(73) Assignee: Topcon Corporation, Tokyo (JP)

( * ) Notice: Subject to any disclaimer, the term of this patent is extended or adjusted under 35 U.S.C. 154(b) by 190 days.

(21) Appl. No.: 10/353,061

(22) Filed: Jan. 29, 2003

(65) Prior Publication Data

US 2003/0164923 A1 Sep. 4, 2003

(30) Foreign Application Priority Data

Feb. 1, 2002 (JP) ........................................ 2002-025597

(51) Int. Cl.[7] ................................................ A61B 3/10
(52) U.S. Cl. ...................................................... 351/216
(58) Field of Search ........................... 351/208, 21, 212, 351/216, 219, 221, 222, 246; 600/407, 476, 544, 558, 595; 434/236; 607/345

(56) References Cited

U.S. PATENT DOCUMENTS

| 4,105,302 | A | 8/1978 | Tate, Jr. |
| 5,052,401 | A | 10/1991 | Sherwin |
| 5,523,809 | A | 6/1996 | Kohayakawa |
| 6,206,702 | B1 * | 3/2001 | Hayden et al. ............. 434/236 |
| 6,338,559 | B1 | 1/2002 | Williams et al. |
| 6,685,318 | B2 * | 2/2004 | Kohayakawa ............... 351/208 |
| 6,722,767 | B2 * | 4/2004 | Dick et al. .................. 351/211 |

FOREIGN PATENT DOCUMENTS

| GB | 2 129 963 A | 5/1984 |
| JP | 2002-17672 A | 1/2002 |

OTHER PUBLICATIONS

Hiroshi Uozato, "Photorefraction Methods and Their History", *Atarashii Ganka* (New Ophthalmology), vol. 7, No. 6, 1990, pp. 823–833.

* cited by examiner

*Primary Examiner*—George Manuel
(74) *Attorney, Agent, or Firm*—Foley & Lardner LLP

(57) ABSTRACT

A device comprises a refraction correcting part 700 for correcting refraction of an eye 400 to be examined of a subject; an adjusting state measuring part 800 for measuring whether a target observed by the eye 400 through the refraction correcting part 700 is in the adjustable range of the eye; and corrective value correcting means 360 for correcting a corrective value for the refraction correcting part 700 so that said eye can achieve best correction based on a result of measurement by the adjusting state measuring part 800, and is configured to measure visual acuity characteristics of the eye 400 at a corrective value for the refraction correcting part 700 to achieve best correction of the eye 400 according to responses of the subject about displayed targets.

23 Claims, 11 Drawing Sheets

(A)

(B)

(A)

(B)

(A)

(B)

BEST CORRECTED VISUAL ACUITY CHARACTERISTICS MEASURING DEVICE, BEST CORRECTED VISUAL ACUITY CHARACTERISTICS MEASURING METHOD, CONTRAST SENSITIVITY MEASURING DEVICE, CONTRAST SENSITIVITY MEASURING METHOD, AND CONTRAST SENSITIVITY TARGET DISPLAYING DEVICE

BACKGROUND OF INVENTION

1. Field of the Invention

The present invention relates to a best corrected visual acuity characteristics measuring device and a best corrected visual acuity characteristics measuring method suitable for use in measuring visual acuity characteristics of an eye with best correction.

The present invention also relates to a contrast sensitivity measuring device and a contrast sensitivity measuring method suitable for precisely determining the contrast sensitivity of a subject at the time of a refractive surgery or improvement of visual acuity with glasses or contact lenses.

The present invention further relates to a contrast target displaying device which can measure contrast sensitivity of an eye to be examined with best correction.

2. Description of Prior Art

A contrast sensitivity measuring device is used to precisely determine the effect of the ocular aberration of a subject on its visual function at the time of a refractive surgery or improvement of visual acuity with glasses or contact lenses. The measurement of contrast sensitivity is conducted on the premise that the corrective value obtained in a frame test (lens exchange method) is a value for best correction. In case of the lens change method, it is based on subjective vision test.

However, in a frame test, an eye is regarded as being best corrected when it obtains a visual acuity of 1.5 or higher in decimal visual acuity since the subject can obtain corrected visual acuity necessary for daily life. For example, there are many cases where a subject having an eye which needs −4.5 diopters for best correction can obtain a decimal visual acuity of 1.5 with a −3.75 diopter correction in a frame test. Thus, in a frame test, a value on the under-correction side may be regarded as the value for best correction. The "best correction" is a state where an eye to be examined focuses at infinity without adjustment.

In a clinical site, contrast sensitivity is used to distinguish eyes with lesions such as ametropia, cataract or keratoconus from normal eyes. When an eye is under-corrected, the maximum value of its luminance contrast sensitivity may not be obtained in a contrast sensitivity test. Namely, in the case where the visual acuity corrected based on a test result by a lens exchange method is not the best corrected visual acuity but an under-corrected visual acuity, when the eye is measured for contrast sensitivity wearing a frame spectacles with a corrective value obtained by the test, the eye may be estimated to have abnormally low contrast sensitivity. Then, a clinical technologist or ophthalmologist may judge there is abnormality in, for example, the visual nerve system behind the retina. As a result, a retest is conducted on a normal eye which has normal contrast sensitivity when best corrected on the premise that the eye has a lesion, resulting in increase in medical cost due to double inspection.

The "best correction" herein includes a slightly over-corrected state as well as the ideal best corrected state because an eye can obtain the maximum visual acuity value by adjustment when slightly over-corrected. When under-corrected, an eye can never obtain a visual acuity which is higher than the corrected value since an image blurs.

SUMMARY OF THE INVENTION

The present invention has been made to overcome the above problems. A first object of the present invention is to provide a best corrected visual acuity characteristics measuring device and a best corrected visual acuity characteristics measuring method by which visual acuity characteristics of an eye can be measured with best correction.

A second of object of the present invention to provide a contrast sensitivity measuring device and a contrast sensitivity measuring method by which visual acuity characteristics of an eye can be measured with best correction.

A third object of the present invention is to provide a contrast target displaying device which can measure contrast sensitivity of an eye to be examined with best correction.

In accomplishing the above objects, a device for measuring best corrected visual acuity characteristics of the present invention comprises, as shown in FIG. 1, a refraction correcting part 700 for correcting refraction of an eye 400 to be examined of a subject; an adjusting state measuring part 800 for measuring whether a target observed by the eye 400 through the refraction correcting part 700 is in the adjustable range of the eye; and corrective value correcting means 360 for correcting a corrective value for the refraction correcting part 700 so that the eye 400 can achieve best correction based on a result of measurement by the adjusting state measuring part 800, and configured to measure visual acuity characteristics of the eye 400 at a corrective value for the refraction correcting part 700 to achieve the best correction of the eye 400 according to responses of the subject about displayed targets.

In a device constituted as above, the adjusting state measuring part 800 measures whether a target observed by the eye 400 through the refraction correcting part 700 is in the adjustable range of the eye 400 to judge whether the refraction of the eye 400 is best corrected, under-corrected or over-corrected by the refraction correcting part 700. Then, the corrective value correcting means 360 corrects the corrective value for the refraction correcting part 700 so that the eye can 400 achieve best correction. Thereby, visual acuity characteristics of the eye 400 can be measured at a corrective value for the refraction correcting part 700 to achieve the best correction of the eye 400 according to responses of the subject about displayed targets.

Preferably, the adjusting state measuring part 800 comprises: a light source 812 for measurement located in a position generally corresponding to targets observed by the eye, a diaphragm part 806 provided in a position conjugate with the light source 812 for measurement, and a light receiving optical system having a light receiving part 810 for receiving luminous flux which has passed through the diaphragm part 806. Then, since the eye 400 is synchronized with the refraction correcting part 700, the measurement on whether the eye 400 is best corrected, under-corrected or over-corrected can be accurately performed.

Preferably, the adjusting state measuring part 800 comprises: a light source 812 for measurement located to be able to emit luminous flux toward the eye 400 while the eye 400 is observing a target; a diaphragm part 806 provided in a position conjugate with the light source 812 for measurement, and a light receiving element 810 arranged to receive luminous flux emitted from the light source 812 for measurement and reflected on the anterior segment 401 of the eye 400 which has passed through the diaphragm part 806 and to be conjugate with the anterior segment 401 of the eye 400, and configured to measure at least one of the size and shape of the opening of the iris in said anterior segment 401 of the eye 400 or at least one of the size and shape of the pupil region of the eye 400 by processing an image of the anterior segment 401 of the eye 400 received by the light receiving element 810. Then, it is possible to check whether a target has brightness suitable to perform optometry by the size of the opening of the iris or the pupil region and to prevent a target from being excessively bright or dark.

Preferably, the adjusting state measuring part 800 comprises: a light source 812 for measurement located to be able to emit luminous flux toward the eye 400 while the eye 400 is observing a target, a diaphragm part (aperture stop) 806 provided in a position conjugate with the light source 812 for measurement; a light receiving optical system having a light receiving part 810 for receiving luminous flux which has passed through the diaphragm part 806, and a polarizing beam splitter 806 for separating luminous flux from the light source 812 for measurement and luminous flux to the diaphragm part 806, wherein the light receiving part 810 is arranged to receive luminous flux emitted from the light source 812 for measurement and reflected on the anterior segment 401 of the eye 400 and to be conjugate with the anterior segment 401 of the eye 400. Then, since the axis of the light beam emitted from the light source 812 and the axis of the light beam which the light receiving part 810 can be coincident with each other by the polarizing beam splitter, the adjusting state measuring part 800 can be downsized.

Preferably, the refraction correcting part 700 is configured to set a value corrected to the minus side by a specified lens refractive index based on corrected visual acuity data of the eye 400. Then, the eye 400 can be best corrected when it is under-corrected based on a subjective optometry using Landolt rings.

Preferably, the refraction correcting part 700 is configured to correct at least one of the specified lens refractive index, astigmatism degree and astigmatic axis and to set a value correct to the minus side with respect to the measurement error of the corrected lens refractive index, astigmatism degree or astigmatic axis based on corrected visual acuity data of the eye 400. The "set with respect to the measurement error" herein means to determine a permissible range of the value to be corrected to the minis side based on the measurement accuracy. Thereby, criteria for the necessary minimum corrective value are determined, and the accuracy of corrective amount of the specified lens refractive index, astigmatism degree or astigmatic axis to achieve best correction of the eye 400 can be determined.

In accomplishing the above objects, a method for measuring best corrected visual acuity characteristics of the present invention comprises, as shown in FIG. 2, a step in which a refraction correcting part 700 corrects the refraction of an eye 400 to be examined of a subject based on corrected visual acuity data of the eye (S102 and S104); a step of displaying a target to the eye 400 through the refraction correcting part 700 (S106); a step in which an adjusting state measuring part 800 measures whether the target is in the adjustable range of the eye 400 (S108 and S110); a step of correcting a corrective value for the refraction correcting part 700 so that the eye 400 can achieve best correction based on a result of measurement by the adjusting state measuring part 800 (S112), and a step of measuring visual acuity characteristics of the eye 400 at a corrective value for the refraction correcting part 700 to achieve the completely correction of the eye 400 according to responses of the subject about displayed targets (S114 to S120).

In accomplish the above objects, a device for measuring contrast sensitivity of the present invention comprised, as shown in FIG. 5, a refraction correcting part 700 for correcting refraction of an eye 400 to be examined of a subject; a contrast target display part 110 for displaying contrast targets; an adjusting state measuring part 800 for measuring whether a contrast target is in the adjustable range of the eye 400 when the eye 400 looks at the target displayed in the contrast target display part 100 through the refraction correcting part 700, a corrective value correcting means 360 for correcting a corrective value for the refraction correcting part 700 so that the eye 400 can achieve best correction based on a result of measurement by the adjusting state measuring part 800, and a contrast sensitivity determining part 390 for determining contrast sensitivity according to responses of the subject about contrast targets displayed through the refraction correcting part 700 corrected by the corrective value correcting means 360.

Preferably, the adjusting state measuring part 800 comprises a light source 812 for measurement located in a position generally corresponding to targets observed by the eye 400; a diaphragm part 806 provided in a position conjugate with the light source 812 for measurement, and a light receiving optical system having a light receiving part 810 for receiving luminous flux which has passed through the diaphragm part 806. Then, the measurement on whether the eye 400 is best corrected, under-corrected or over-corrected can be accurately performed.

When the light receiving part 810 is configured to be generally conjugate with the anterior segment of the eye 400 and capable of measuring the size or shape of the pupil of the eye 400 by image processing using an output of the light receiving part 810, it is suitably used to keep the retinal luminance constant or useful in measurement conducted keeping the area of a pupil region constant. The size and shape of the pupil is useful for simulation of fundus images or modulation transfer function.

In accomplish the above objects, a method for measuring contrast sensitivity of the present invention comprises, as shown in FIG. 6 and FIG. 7, a step in which a refraction correcting part 700 corrects the refraction of an eye 400 to be examined of a subject based on corrected visual acuity data (spherical degree, astigmatism degree and astigmatism axis) of the eye 400 (S302 and S304); a step of displaying a contrast target to the eye 400 through the refraction correcting part 700 (S306); a step in which an adjusting state measuring part 800 measured whether the contrast target is in the adjustable range of the eye 400 (S308 and S310); a step of correcting a corrective value for the refraction correcting part 700 so that the eye 400 can achieve best correction based on a result of measurement by the adjusting state measuring part 800 (S312), and a step of measuring contrast sensitivity of the eye 400 at a corrective value for the refraction correcting part 700 to achieve the best correction of the eye 400 according to responses of the subject about displayed contrast targets (S314 to S324).

In accomplishing the above objects, a device for displaying contrast sensitivity targets of the present invention comprises, as shown in FIG. 5, a refraction correcting part 700 for correcting refraction of an eye 400 to be examined of a subject; a contrast target display part 110 for displaying contrast targets; an adjusting state measuring part 800 for measuring whether a contrast target is in the adjustable range of the eye 400 when the eye 400 looks at a target displayed in the contrast target display part 110 through the refraction correcting part 700; a contrast sensitivity determining part 390 for determining contrast sensitivity according to responses of the subject about displayed contrast targets, and corrective value correcting means for correcting a corrective value for the refraction correcting part 700 so that the eye 400 can achieve best correction based on a result of measurement by the adjusting state measuring part 800, wherein the contrast target display part 110 is configured to display contrast targets to measure contrast when the contrast target is judged to be in the adjustable range of the eye 400 by the adjusting state measuring part 800.

This application is based on Japanese patent applications, No. 2002-025597 filed in Japan on Feb. 1, 2002, which are entirely incorporated herein by reference.

The present invention will become more fully understood from the detailed description given hereinbelow. However, the detailed description and the specific embodiment are illustrated of desired embodiments of the present invention and are described only for the purpose of explanation. Various changes and modifications will be apparent to those ordinary skilled in the art on the basis of the detailed description.

The applicant has no intention to give to public any disclosed embodiment. Among the disclosed changes and modifications, those which may not literally fall within the scope of the patent claims constitute, therefore, a part of the present invention in the sense of doctrine of equivalents.

BRIEF DESCRIPTION OF THE DRAWINGS

Other objects, features and advantages of the present invention will become apparent from the detailed description of the preferred embodiments of the invention which follows, when considered in the light of the accompanying drawings, in which.

DESCRIPTION OF THE PREFERRED EMBODIMENTS

Figure 1:
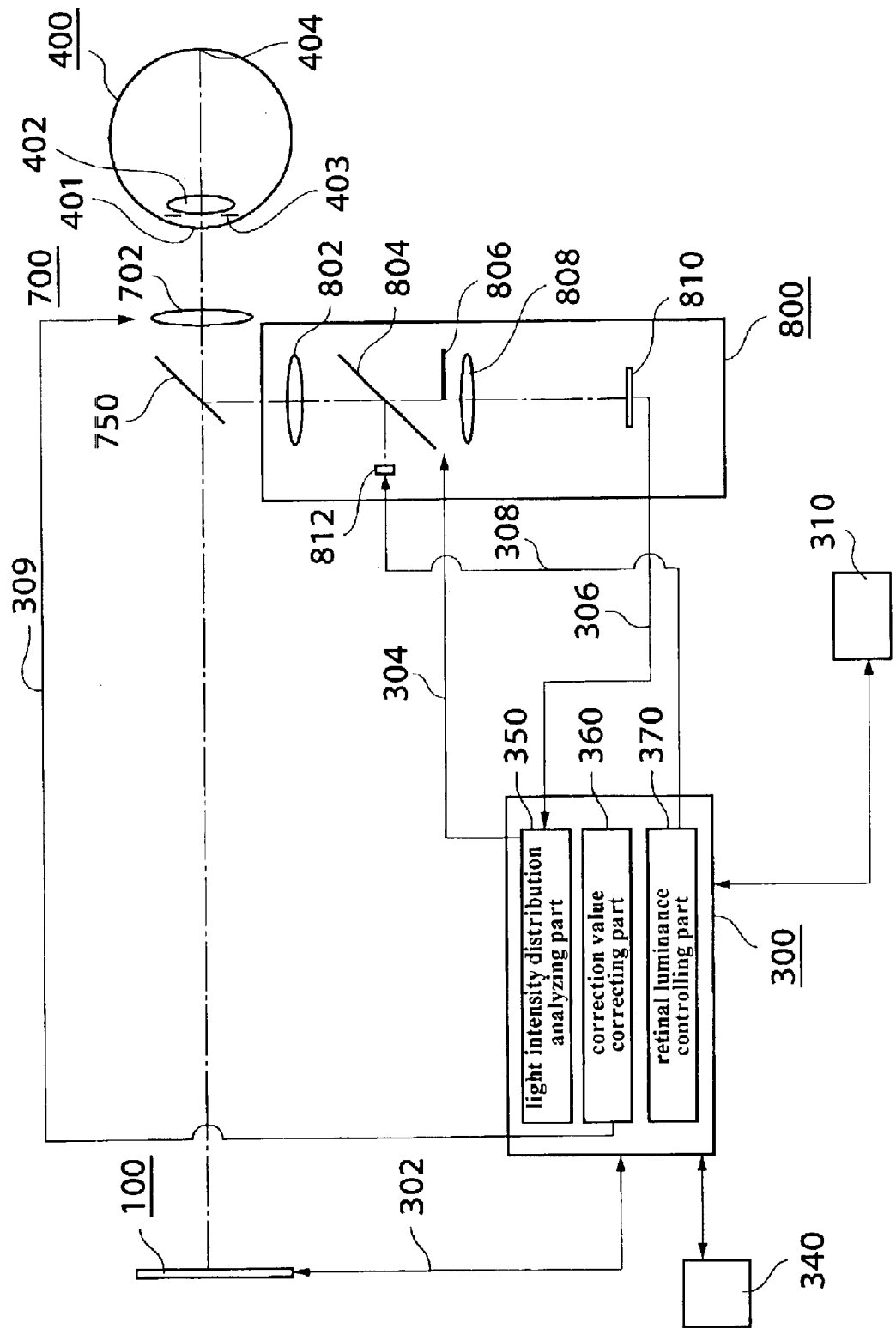
FIG. 1 is a block diagram for explaining a first embodiment of the present invention.

Description will be hereinafter made of the embodiments of the present invention with reference to the drawings. In the drawings, the same or corresponding members are designated by the same or similar numerals, and overlapping descriptions are omitted. FIG. 1 is a block diagram for explaining a first embodiment of the present invention.

In FIG. 1, a target display unit 100 is a device for displaying targets for measuring visual acuity characteristics of an eye 400 to be examined such as Landolt rings for measuring general visual acuity or targets for measuring contrast sensitivity, and may be a monitor type device or a space saving type device employing a filter system. The target display unit 100 is located 1 m (1.0 in spectacle diopter) away from, for example, a horopter lens 702. The display of targets in the target display unit 100 is performed by control signals from a central arithmetic unit 300.

As anatomically known, an eye 400 to be examined of a subject has an anterior segment 401 including a cornea, a lens 402, an iris 403 and a fundus oculi 404 including a retina.

A horopter 700 as a refraction correcting part is a device capable of arbitrarily varying the spherical degree, astigmatism degree and axis direction of the horopter lens 702, and referred to also as "vision optometric device". The horopter 700 is configured to exchange spherical lenses and toric lenses automatically to vary the spherical degree, astigmatism degree and axis direction of the horopter lens 702. The control for correcting the refraction of the horopter lens 700 is performed by corrective value correcting means 360 provided in the central arithmetic unit 300.

A dichroic mirror 750 is an optical member for directing visible light and infrared ray (940 nm, for example) in the light from the eye 400 to a target and a refraction measuring unit 800, respectively. While the eye 400 is observing a target displayed in the target display unit 100, the refraction measuring unit 800 measures the adjusting state of the eye 400 using infrared ray. At the time of the measurement, the refraction measuring unit 800 does not prevent the eye 400 to from watching the target since it uses infrared ray. When infrared ray of about 800 nm wavelength having high spectral luminous efficacy is used, a light source 812 for photo refraction of the refraction measuring unit 800 can be turned off during the measurement of contrast sensitivity so as not to affect the measurement.

The refraction measuring unit 800 as an adjusting state measuring part comprises a lens 802, a polarizing beam splitter 804, a diaphragm 806 for photo refraction as a diaphragm part, a conjugate lens 808, an image pickup element 810 as a light receiving part and the light source 812 for photo refraction as a light source for measurement. The lens 802 is one for making the fundus oculi 404 and the light source 812, and the fundus oculi 404 and the diaphragm 806 geometric-optically conjugate with each other when the eye 400 focuses on the target display unit 100 through the horopter lens 702. "Conjugate" herein means the relation between object and image in image formation in the geometrical optics sense. When two things are conjugate with each other, they can exchange their roles. For example, a light beam in object space and a corresponding light beam in image space are conjugate with each other.

The polarizing beam splitter 804 reflects s-polarized light and transmits p-polarized light, for example, and has a function of an isolator. Thereby, reflected light from the fundus oculi 404 is transmitted to the diaphragm 806 but unnecessary reflected lights (namely, noises) from the cornea 401, horopter lens 702 and lens 802 are not. The diaphragm 806 for photo refraction is a half space diaphragm provided in the optical axis toward the image pickup element 810.

The conjugate lens 808 is a lens for making the iris 403 of the eye 400 conjugate with the image pickup element 810 through refracting members such as the cornea 401, horopter lens 702, and the lens 802. The conjugate lens 808 permits measurement of the light intensity distribution on the pupil region of the eye 400. The light source 812 generates near-infrared light (940 nm, for example) so that the measurement of the adjusting state of the eye 400 may not interfere with the observation of a target by the eye 400. Although the diaphragm 806 and the light source 812 have an orientation, when the diaphragm 806 is turned 90°, astigmatism component of the eye 400 can be measured.

The central arithmetic unit 300, which is a personal computer mounting Pentium (trademark) or Celeron (trademark) manufactured by Intel Corporation as a CPU, exhibits various functions when used with various LSIs and software. The central arithmetic unit 300 has input devices 310 and 340, a light intensity distribution on pupil region analyzing part 350, a corrective value correcting part 360 and a retinal luminance control part 370. The input device 310, which is used by a subject to input results of recognition of targets and so on, has two or four buttons so that the subject can easily answer on which side (right or left), or in which position (top, bottom, right or left) a target is displayed. The input device 340 is used by a clinical technologist or ophthalmologist to input the ID number, name, sex and so on of the subject (a patient in most cases) and comprises a keyboard, a pointing device and so on.

The light intensity distribution on pupil region analyzing part 350 extracts a signal of the light intensity distribution on the pupil region of the eye 400 from an image signal picked up by the image pickup element 810 to measure the gradient of the light intensity distribution of the eye 400. As described in detail later, the gradient of the light intensity distribution is a parameter which relates to the focus position of the eye 400 and the position of the target display unit 100 and which is necessary to calculate an adjusting diopter necessary to achieve best correction of the eye 400 from the current correction.

The corrective value correcting part 360 corrects the corrective value for the horopter 700 so that the eye 400 can achieve best correction based on the result of analysis by the light intensity distribution on pupil region analyzing part 350.

The retinal luminance control part 370 sends a control signal to the light source 812 so that the luminance on the retina located at fundus oculi 404 of the eye 400 may be constant.

A display part control line 302 is a control line for sending a control signal from the central arithmetic unit 300 to the target display part 100. A diaphragm control line 304 is a control line for sending a control signal from the central arithmetic unit 300 to the diaphragm 806. A CCD signal line 306 is a signal line for sending an image signal picked up by the image pickup element 810 to the light intensity distribution on pupil region analyzing part 350. A light source control line 308 is a control line for sending a control signal from the central arithmetic unit 300 to the light source 812. A horopter control line 309 is a signal line connecting a control signal from the corrective value correcting part 360 with the horopter 700.

Figure 2:
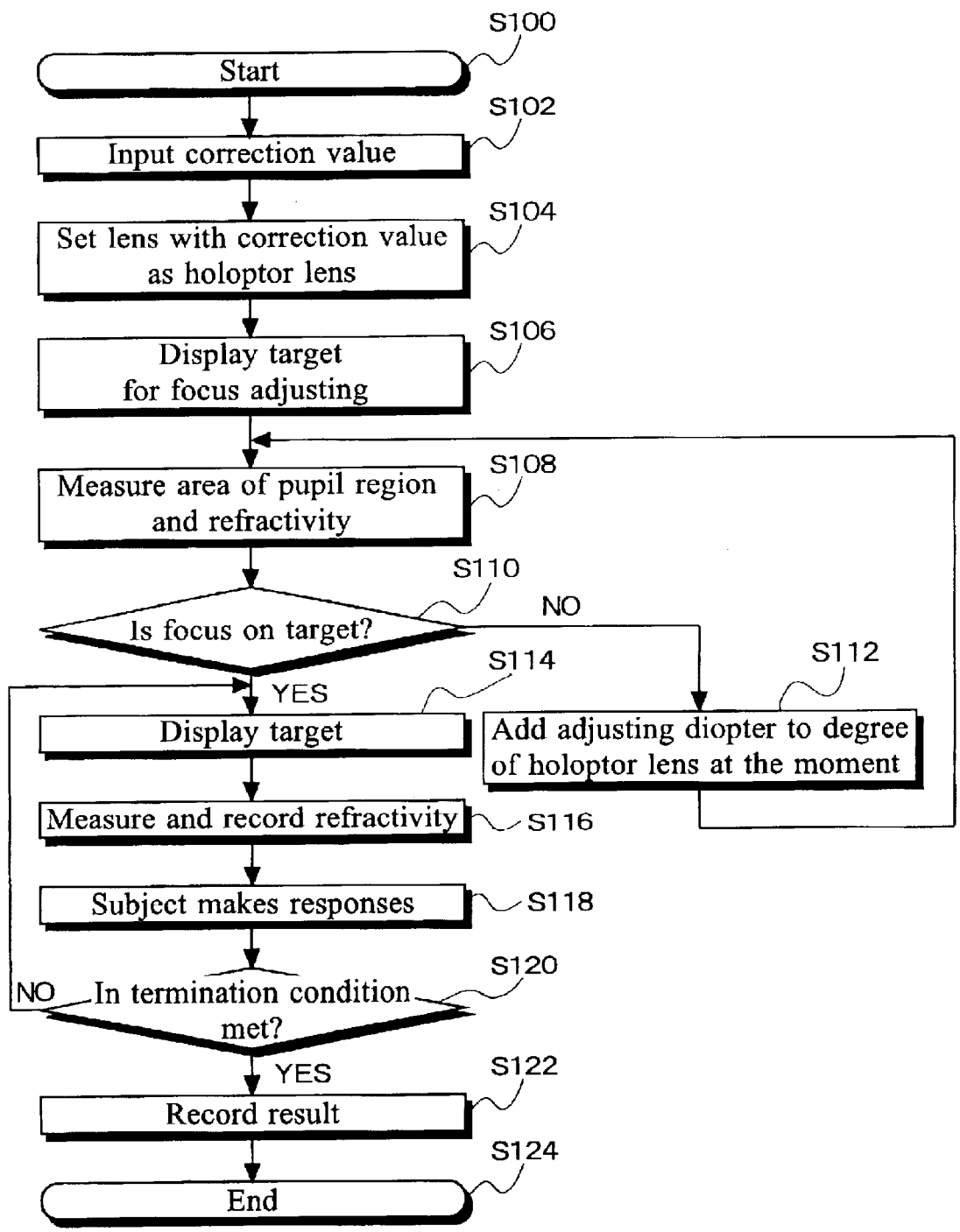
FIG. 2 is a flowchart for explaining the procedure for measuring visual acuity characteristics of an eye to be examined with a device shown in FIG. 1.

Description will be next made of the operation of the device constituted as above. FIG. 2, which is a flowchart for describing the procedure for measuring the visual acuity characteristics of an eye to be examined in the device shown in FIG. 1, describes the measurement of visual acuity characteristics of an eye with best correction.

First, a clinical technologist or the like input a corrective value for an eye 400 to be examined of a subject with the input device 340 (S102). Then, the central arithmetic unit 300 sends a lens exchange signal to the horopter 700 through the horopter control line 309 to set a lens having the corrective value in the horopter 700 (S104). The central arithmetic unit 300 then sends a target display signal to the target display unit 100 through the display part control line 302 to display a target for focus adjusting (S106).

The area of the pupil region of the eye 400 is measured, and the refraction measuring unit 800 measures the refractivity of the eye 400 (S108). At this time, the light intensity distribution on pupil region analyzing part 350 judges whether the focus of the eye 400 is on the target or not (S110). When the focus is not on the target, an adjusting diopter, for example −0.1 to −1.0 diopter, is added to the degree of the horopter lens 702 at the moment by a control signal from the corrective value correcting part 360 (S112), and the process is returned to S108. When the focus in on the target, the target display unit 100 a displays target for measuring visual acuity characteristics (S114). Then the refraction measuring unit 800 measures the refraction of the eye 400 at the time of display of the target for measuring visual acuity characteristics and records the thus measured refraction (S116). The subject makes a response about the displayed target (S118), and a judgment is made on whether the response result meets the termination condition (S120). When the response result does not meet the termination condition, the process returns to S114. The response result of the subject meets the termination condition, the result is recorded (S122) and the measurement of the visual acuity characteristics of the eye 400 at the corrective value for the horopter lens 702 to achieve best correction thereof is completed (S124).

Figure 3:
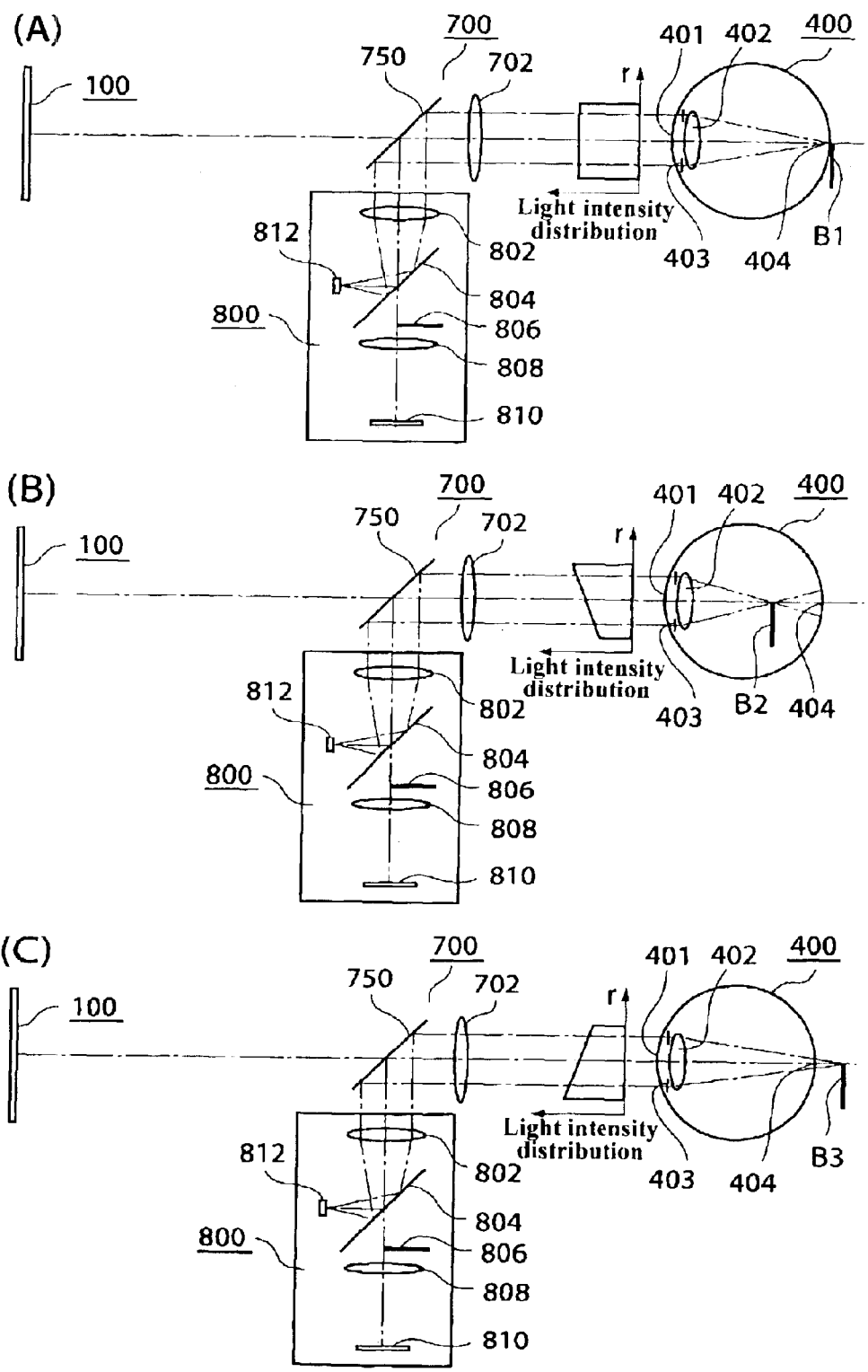
FIG. 3 is a view for explaining the principle of the analysis of light intensity distribution on a pupil region.

FIG. 3 illustrates the principle of the analysis of light intensity distribution on a pupil region by the light intensity distribution on pupil region analyzing part, in which (A) illustrates an eye with best correction, (B) illustrates a state where a nearsighted eye is under-corrected, and (c) illustrates a state where a nearsighted eye is over-corrected. Here, description will be made of the principle of obtaining refraction from light intensity distribution on a pupil region, namely photo refraction. There are two photo refraction; a method in which a light source is located on the optical axis and a method in which a light source is located off the optical axis. The latter, which is advantageous when the point at which the subject is looking at is approximately positioned at a conjugate position of the light source, will be described here. In photo refraction, an illuminating light source is provided at a position on the optical axis and a half space diaphragm 806 is located in a light receiving system which is conjugate with the illuminating light source. The refraction of an eye is examined from distribution of reflected light from the fundus oculi thereof which appears in the pupil region thereof. A judgment is made on whether the eye is under-corrected or over-corrected by whether a bright portion of the reflected light from the fundus oculi is on the same side or opposite side as the diaphragm. With best correction, the light intensity distribution in the light path from the dichroic mirror 750 to the eye 400 is uniform irrespective of the distance r from the optical axis. In FIG.

3, the line segment B1 represents the location of the image on the fundus oculi 404.

With undercorrection, the light intensity in the light path from the dichroic mirror 750 to the eye 400 increases as the distance r from the optical axis increases on the side of the diaphragm and decreases as the distance r from the optical axis increases on the other side. In FIG. 3, the line segment B2 represents the location of the image in the eye 400. On the other hand, with overcorrection, the light intensity in the light path from the dichroic mirror 750 to the eye 400 decreases as the distance r from the optical axis increases on the side of the diaphragm and increases as the distance r from the optical axis increases on the other side. In FIG. 3, the line segment B3 represents the location of the image outside the eye 400.

Then, when the eye is best corrected by the horopter 700, the light intensity distribution becomes flat when the eye 400 focuses on the target display unit 100. Also, the light intensity distribution on pupil region analyzing part 350 can judges whether the eye 400 to is looking at a point closer or farther than the target display unit 100 using the gradient of the light intensity distribution as a parameter. The light intensity distribution on pupil region analyzing part 350 also can measure how close or how far the eye 400 is looking from the gradient of the light intensity distribution with an absolute accuracy of about 0.1 to 0.01 diopter.

Figure 4:
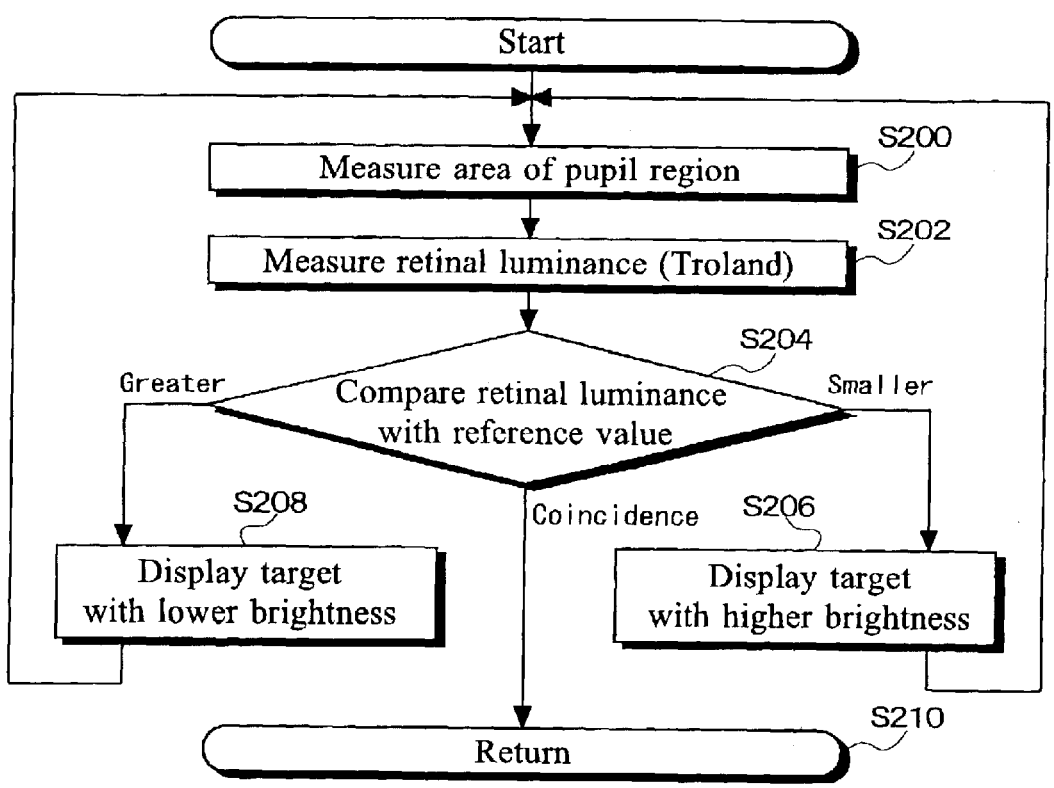
FIG. 4 is a flowchart for explaining the procedure for controlling the luminance on the retina located at fundus oculi of an eye to be examined to be constant.

FIG. 4 is a flowchart for explaining the procedure for the retinal luminance control part to control the luminance on the retina located at fundus oculi of an eye to be examined to be constant. First, the retinal luminance control part 370 measures the area of the pupil region of the eye 400 to be examined from an image signal picked up by the image pickup element 810 (S200), and then measures the retinal luminance (Troland) of the eye 400 from the area of the pupil region thereof and the brightness of the target (S202). The thus measured retinal luminance is compared with a predetermined reference value (S204). When the retinal luminance is smaller than the reference value, a target with high brightness is displayed in the target display unit 100 and the process is returned to S200 (S206). When the retinal luminance is greater than the reference value, a target with a lower brightness is displayed in the target display unit 100 and the process is returned to S200 (S208). When the retinal luminance is substantially equivalent to the reference value, the process goes to Return (S210), and the visual acuity characteristics of the eye to be examined are measured.

Figure 5:
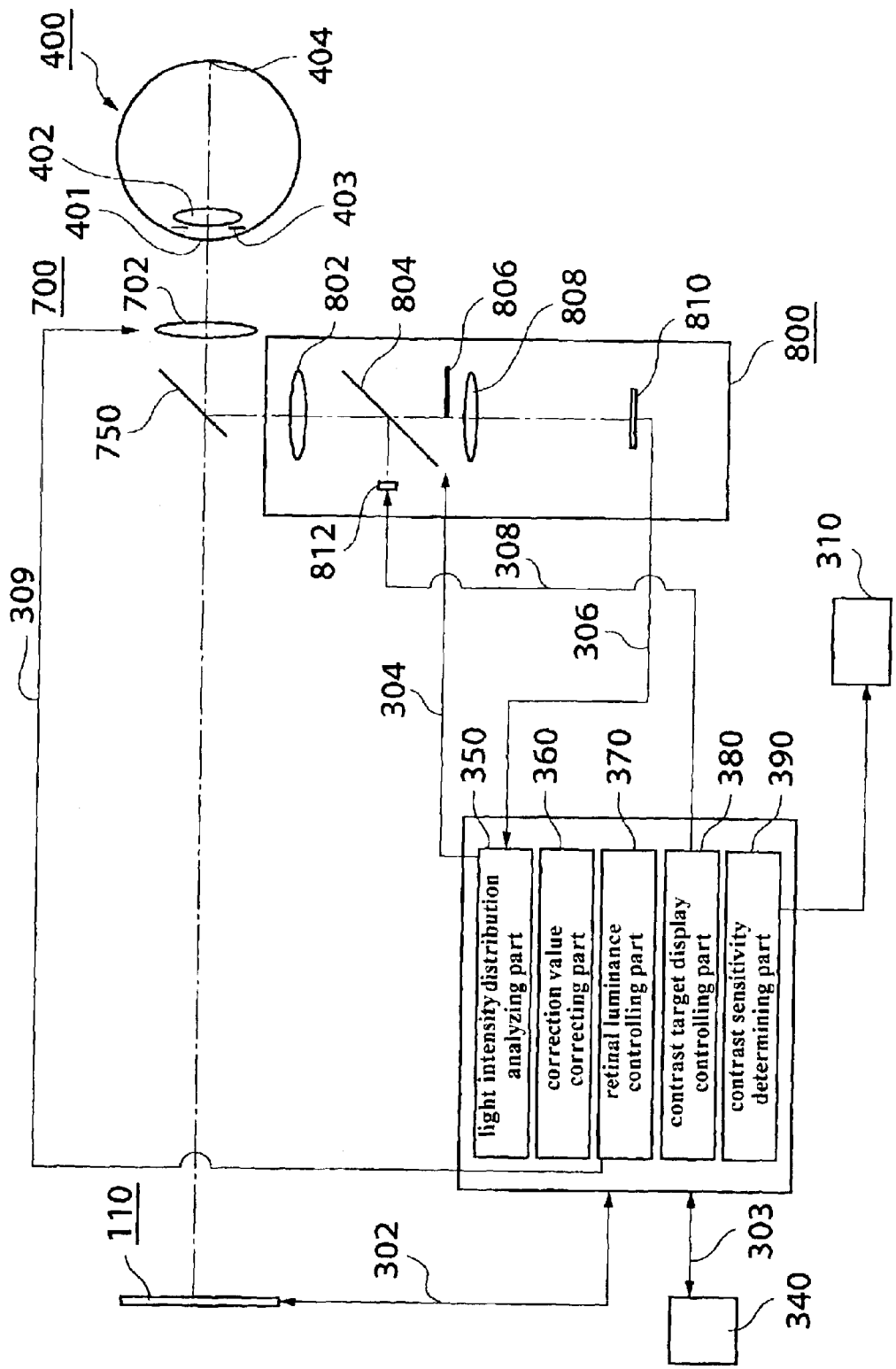
FIG. 5 is a block diagram for explaining a second embodiment of the present invention.

FIG. 5 is a block diagram for explaining a second embodiment of the present invention. In FIG. 5, components having the same function as the components in FIG. 1 are designated by the same reference numerals and the description thereof will be omitted. In this embodiment, a contrast target display part 110 for displaying contrast targets is provided as the target display unit 100. The contrast target display part 110 may be a monitor type device or a space saving type device employing a filter system.

A central arithmetic unit 300 has a contrast target display control part 380 and a contrast sensitivity determining part 390. The contrast target display control part 380 determines a target to be displayed in the contrast target display part 110 and sends a contrast target display control signal to the contrast target display unit 110 through a display control signal line 303 according to a prescribed sequence for measurement of contrast sensitivity. The contrast sensitivity determining part 390 determines the contrast sensitivity of an eye to be examined based on the responses of the subject about targets displayed in the contrast target display part 110.

Figure 6:
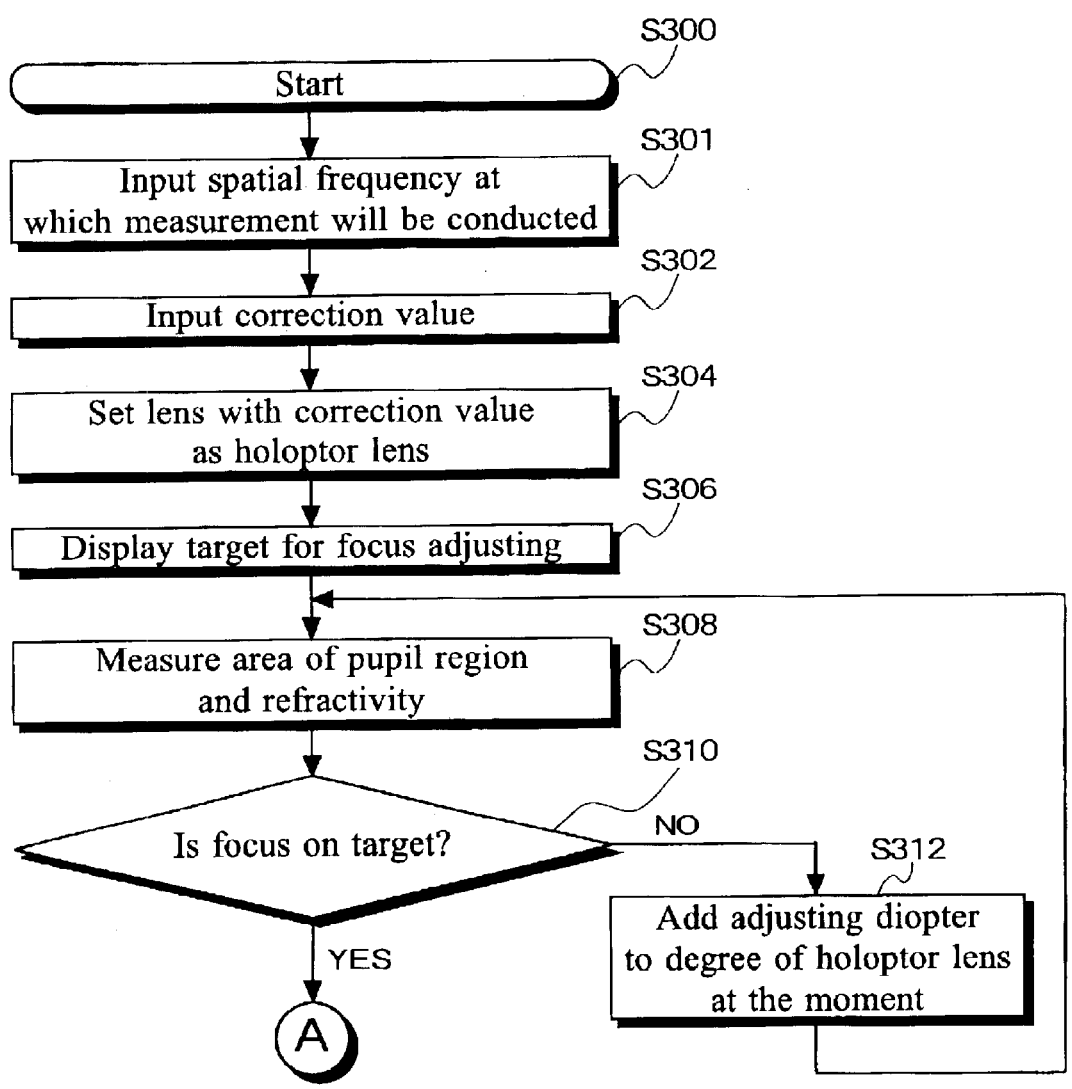
FIG. 6 is a flowchart for explaining the procedure for measuring contrast sensitivity of an eye to be examined with a device shown in FIG. 5.
Figure 7:
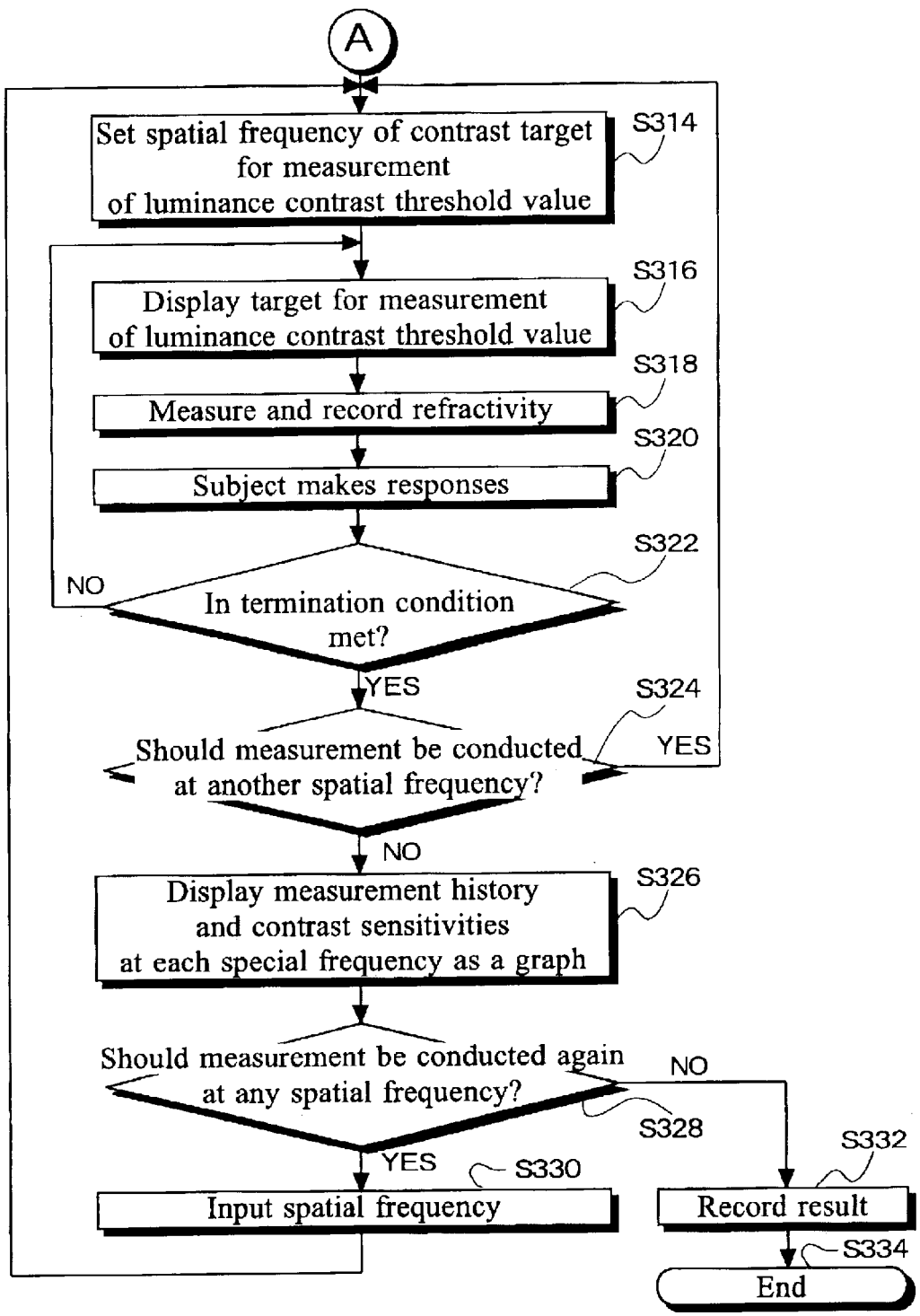
FIG. 7 is a flowchart for explaining the procedure for measuring contrast sensitivity of an eye to be examined, continuing from the flowchart of FIG. 6.

Description will be next made of the operation of the device constituted as above. FIG. 6 and FIG. 7, which are flowcharts for describing the procedure for measuring the contrast sensitivity of an eye to be examined in the device shown in FIG. 5, describe the measurement of contrast sensitivity of an eye with best correction by a horopter lens 700 (for a lens exchange method). First, a clinical technologist or the like inputs a spatial frequency at which the measurement is conducted into the central arithmetic unit 300 (S301) and then inputs a corrective value for the eye 400 to be examined of the subject with the input device 340 (S302). The central arithmetic unit 300 sends a lens exchange signal to the horopter 700 through the horopter control line 309 to set a lens with the corrective value as the horopter lens 702 (S304). Then, the central arithmetic unit 300 sends a contrast target display control signal to the contrast target display part 110 through the display control signal line 303 to display a target for focus adjusting (S306).

Then, the area of the pupil region of the eye 400 is measured, and the refraction measuring unit 800 measures the refraction of the eye 400 (S308). At this time, the light intensity distribution on pupil region analyzing part 350 judges whether the focus of the eye 400 is on the target or not (S310). When the focus is not on the target, an adjusting diopter, for example −0.1 to −1.0 diopter, is added to the degree of the horopter lens 702 at the moment (S312), and the process is returned to S308. Preferably, the adjusting diopter is calculated in the corrective value correcting means 360 using the gradient of light intensity distribution analyzed by the light intensity distribution on pupil region analyzing part 350. The adjusting diopter may be a constant value such as −0.1 diopter. In this case, the clinical technologist or the like determines suitable correction and obtains a corrective value to achive the best correction by try and error.

When the focus of the eye 400 is on the target, the clinical technologist or the like set a spatial frequency of contrast targets for measurement of a contrast luminance threshold value by an up-down method with the input device 340 (S314). The spatial frequency of contrast targets is 3, 6, 12 or 18 cpd [cycles/deg], for example. The measurement is conducted by a psychological measurement method called up-down method. The up-down method is used with a forced choice method in which a target with contrast and a target without contrast are simultaneously displayed once and the subject responses the position where there is a Gabor stimulus. In one display of the contrast sensitivity target, a background is first displayed to the subject, and then a Gabor stimulus is displayed thereto and the response of the subject is recorded. Then, the central arithmetic unit 300 repeatedly displays a Gabor stimulus to the subject until the measurement is completed. Instead of the up-down method, a method of limits, method of adjustment, constant method, PEST, or QUEST may be employed. The time for which one contrast sensitivity target is displayed is 1 to 3 seconds, preferably 2 seconds, from a clinical point of view.

Then, in the contrast target display part 110, a target for measurement of contrast sensitivity designated by the contrast target display control part 380 (S316) is displayed. Then the refraction measuring unit 800 measures the refraction of the eye 400 at the time of display of the target for measuring visual acuity characteristics and records the thus measured refraction (S318). The subject makes a response about the displayed target (S320), and a judgment is made on whether the response result meets the termination condition (S322). When the response result does not meet the termination condition, the process returns to S316. When the response result meets the termination condition at one spatial frequency, a judgment is made on whether measurement is conducted at another spatial frequency (S324). If YES, the process is returned to S314 and setting of a spatial frequency is performed.

When measurement is completed at every spatial frequency at which contrast sensitivity should be measured, the measurement history and the contrast sensitivity at each spatial frequency are displayed as a graph (S326). The clinical technologist or ophthalmologist sees the result displayed as a graph and judges whether there is an abnormality at any of the spatial frequencies. Then, the clinical technologist or ophthalmologist judges whether measurement should be conducted again at any spatial frequency (S328), and, in case of "YES" at S328, inputs a spatial frequency at which measurement is to be conducted (S330). Then the process is returned to S314 (S330). In case of "NO" at S328, when the contrast luminance threshold values of the subject are obtained, the central arithmetic unit 300 stores the results such as the target displaying conditions and the responses of the subject in a file (S332), and the measurement of the contrast sensitivity of the eye 400 at the corrective value for the horopter lens 702 to achieve best correction thereof is completed (S324).

Figure 8:
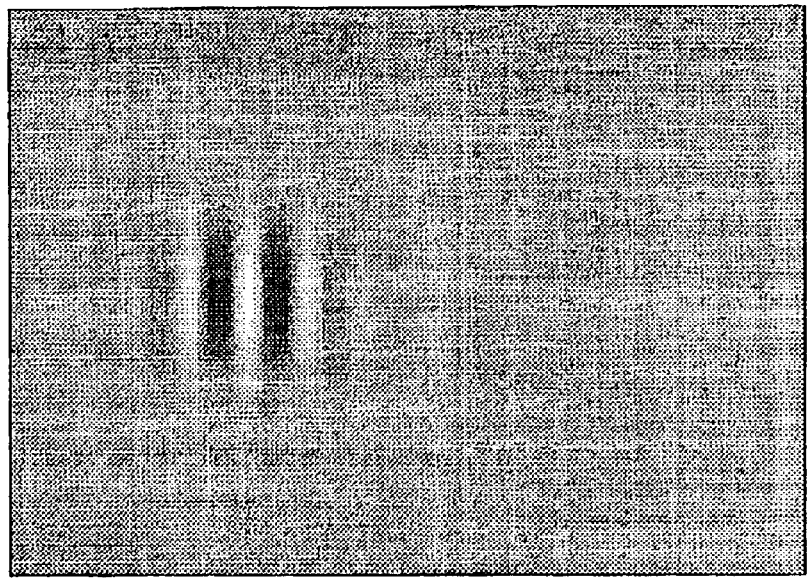
FIGS. 8(A) and (B) are views for explaining a stimulus display pattern for use in an up-down method.
Figure 8:
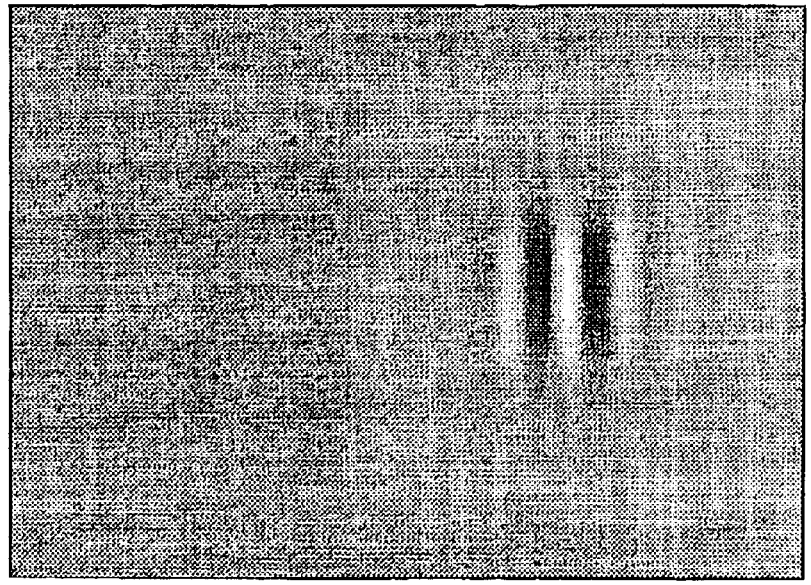

In FIG. 8, displaying examples of targets are shown. In the example shown in FIG. 8(A), a target with high contrast is on the left and a target without contrast is on the right. In the example shown in FIG. 8(B), a target with high contrast is on the right and a target without contrast is on the left.

Figure 9:
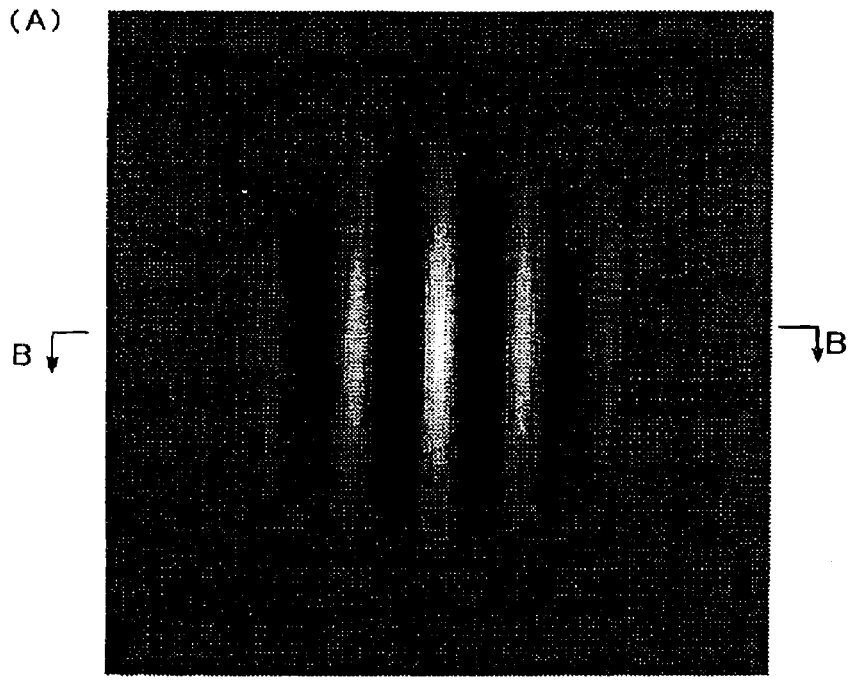
FIGS. 9(A) and (B) illustrate a target with high contrast shown in FIG. 8.
Figure 9:
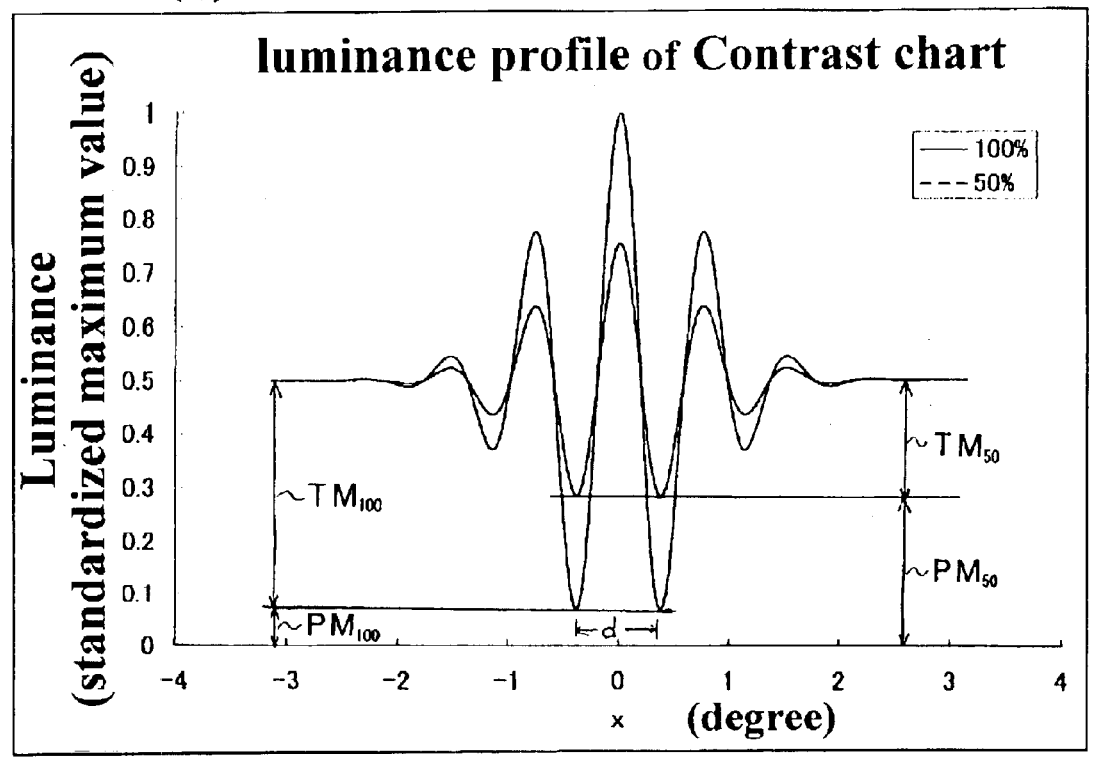

FIG. 9 is view for explaining the target with a large contrast shown in FIG. 8, in which (A) is a plan view of a Gabor stimulus thrown on the anterior segment of a subject, (B) illustrates the luminance profile of the contrast chart in the direction of B—B in (A). The peak interval "d" of the luminance profile corresponds to the spatial frequency.

Figure 10:
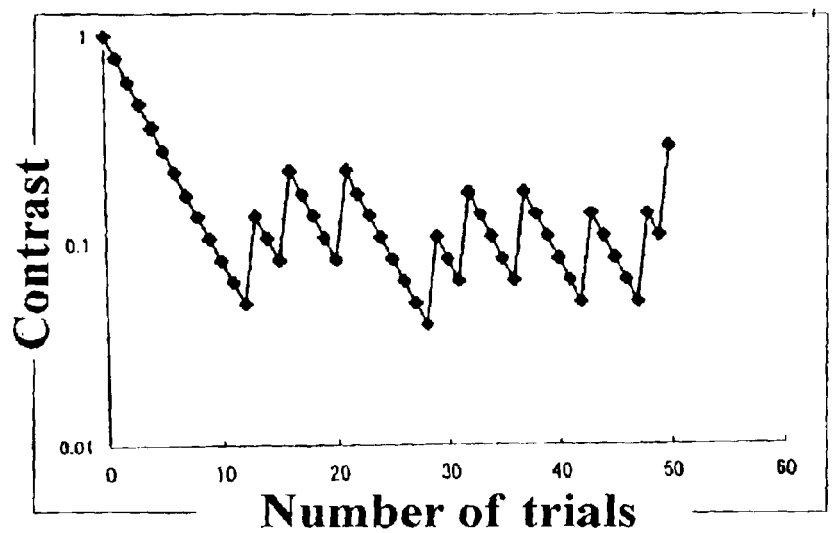
FIG. 10 is a view showing an example of changes of contrast in up-down method.

FIG. 10 is a graph showing an example of the change in contrast in the up-down method, in which the contrast is plotted on the horizontal axis and the number of stimulus on the vertical axis. The measurement is started with a contrast of 100% (shown as 1), and every time the subject responds correctly, the contrast of the stimulus is decreased by 0.1 in logarithm at a time. When the subject responds wrongly, the contrast of the stimulus is increased by four steps. When the subject responds wrongly five times in each ups and downs, the measurement is completed. The contrast threshold value of the subject is the average of the ten contrast threshold values at which the subject responded wrongly, for example 0.06 (=$10^{-1.2}$). The contrast sensitivity of the subject is the reciprocal of the contrast threshold value.

Figure 11:
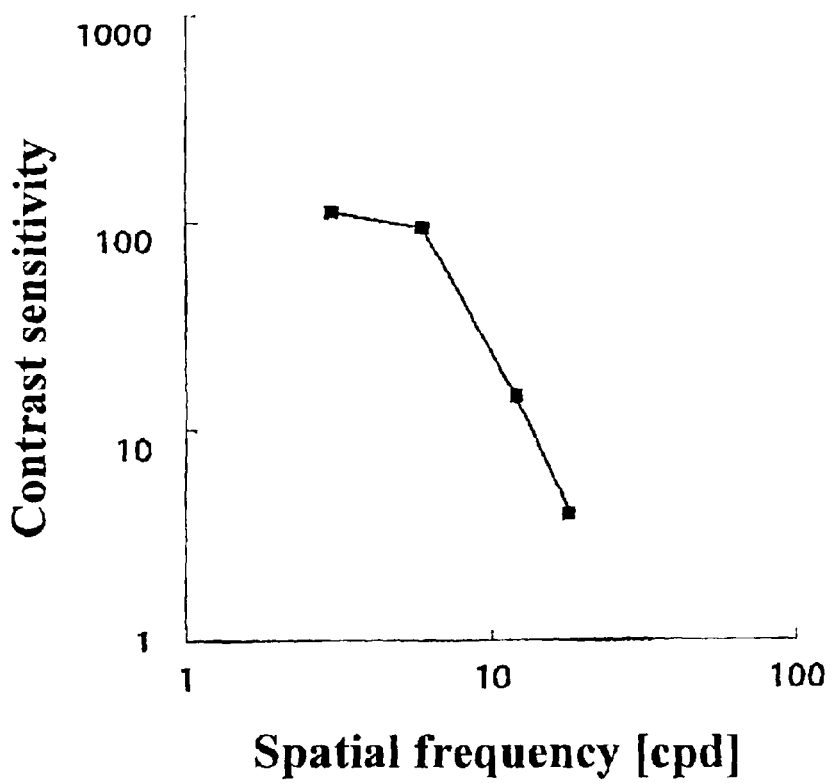
FIG. 11 is a graph showing the relation between the contrast sensitivity and the spatial frequency, and FIGS. 12(A) and (B) are views comparing the contrast sensitivity measured under the best corrected condition and the contrast sensitivity measured under correction based on a subjective optometry.

FIG. 11 is a graph showing the relation between the contrast sensitivity and the spatial frequency. Based on the history of the responses of the subject at various spatial frequencies, the contrast threshold values for each spatial frequency are determined. Then, the central arithmetic unit 300 calculates the reciprocals of the contrast threshold values to obtain the contrast sensitivities. In general, the contrast sensitivity of a subject takes the maximum value when the spatial frequency is in the range of 3 to 6 cpd and tends to decrease gradually when the spatial frequency increases to 10 cpd or higher. When the subject has an abnormal value at some spatial frequencies as compared with a standard pattern of the contrast sensitivity to the spatial frequency, there is a possibility that the subject has a lesion in the pupil or optic nerves. Thus, the measurement of contrast sensitivity is suitable as an optical examination.

Figure 12:
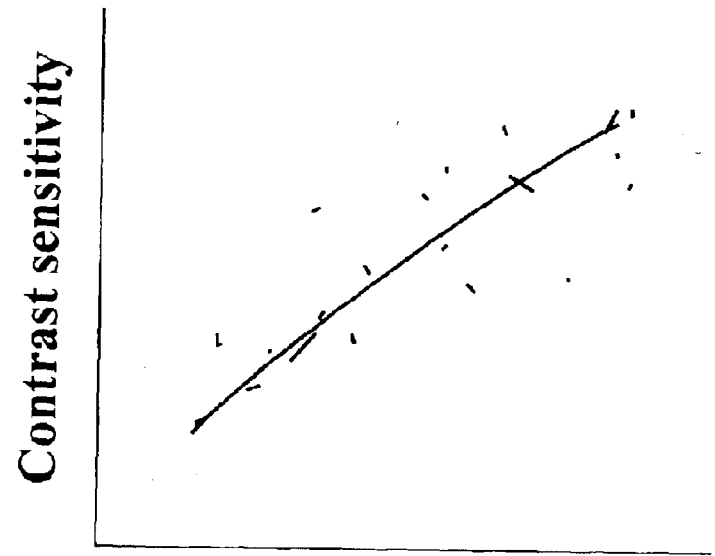
Figure 12:
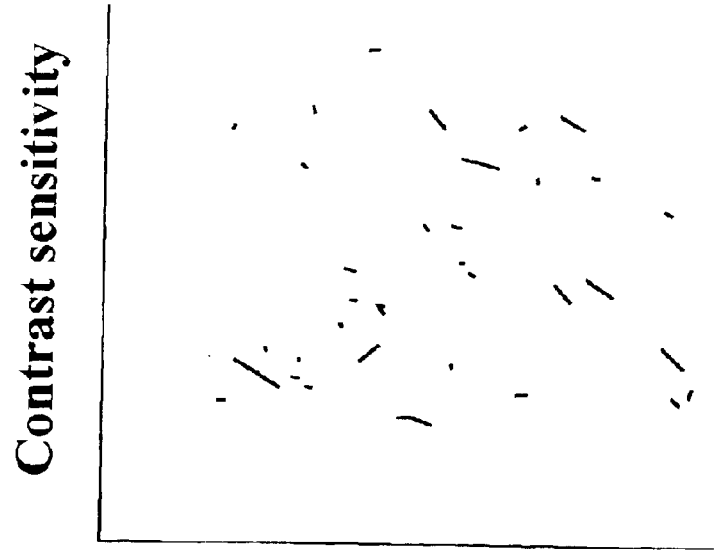

FIG. 12 is a view comparing contrast sensitivity measured with best correction and contrast sensitivity measured with correction based on a subjective optometry, in which (A) shows the contrast sensitivity measured with best correction and (B) shows the contrast sensitivity measured with correction based on a subjective optometry. With best correction, higher-order wavefront aberration quantity and quality measured with a wavefront sensor and contrast sensitivity CS form a regression line. This agrees with the empirical rule that contrast sensitivity decreases with increases of higher-order wavefront aberration quantity.

On the contrary, it has been found by zealous studies by present inventors that eye is under-corrected by −1.0 to −0.1 diopter with correction based on a subjective optometry using Landolt rings in some cases. As a result, there is no correlation between higher-order wavefront aberration quantity measured with a wavefront sensor and contrast sensitivity. In other words, from higher-order wavefront aberration quantity, contrast sensitivity can be predicted for only an eye with best correction. In many cases, contrast sensitivity CS predicted from higher-order wavefront aberration quantity and quality measured with a wavefront sensor does not agree with contrast sensitivity CS with correction based on a subjective optometry since an eye with correction based on a subjective optometry is undercorrected by −1.0 to −0.1 diopter.

Although the refraction measuring unit as an adjusting state measuring part uses infrared ray in the above embodiment, the present invention is not limited thereto. Any device may be used as the refraction measuring unit as long as the optical adjusting state of an eye to be examined can be measured. The photo refraction may be performed by either an optical axis photorefraction method or an off-axis photorefraction method.

As has been described above, the best corrected visual acuity characteristics measuring device of the present invention comprises: a refraction correcting part for correcting refraction of an eye to be examined of a subject; an adjusting state measuring part for measuring whether a target observed by the eye through the refraction correcting part is in the adjustable range of the eye; and corrective value correcting means for correcting a corrective value for the refraction correcting part so that the eye can achieve best correction based on a result of measurement by the adjusting state measuring part, and configured to measure visual acuity characteristics of the eye at a corrective value for the refraction correcting part to achieve the best correction of the eye according to responses of the subject about displayed targets. Thus, the visual acuity characteristics of the eye can be measured not with undercorrection based on, for example, a subjective optometry using Landolt rings but after the corrective value for the refraction correcting part is corrected by the refraction correcting part so that the eye can achieve best correction.

The contrast sensitivity measuring device of the present invention comprises comprising: a refraction correcting part for correcting refraction of an eye to be examined of a subject; a contrast target display part for displaying contrast targets; an adjusting state measuring part for measuring whether a contrast target is in the adjustable range of the eye when the eye looks at the target displayed in the contrast target display part through the refraction correcting part, corrective value correcting means for correcting a corrective value for the refraction correcting part so that the eye can achieve best correction based on a result of measurement by the adjusting state measuring part, and a contrast sensitivity determining part for determining contrast sensitivity according to responses of the subject about contrast targets displayed through the refraction correcting part corrected by the corrective value correcting means. Thus, the contrast sensitivity of the eye can be measured not with undercorrection based on, for example, a subjective optometry using Landolt rings but after the corrective value for the refraction correcting part is corrected by the refraction correcting part so that the eye can achieve best correction.

What is claimed is:

1. A device for measuring best corrected visual acuity characteristics comprising:

a refraction correcting part for correcting refraction of an eye to be examined of a subject;

an adjusting state measuring part for measuring whether a target observed by said eye through said refraction correcting part is in an adjustable range of said eye; and corrective value correcting means for correcting a corrective value for said refraction correcting part so that said eye can achieve best correction based on a result of measurement by said adjusting state measuring part, and configured to measure visual acuity characteristics of said eye at a corrective value for said refraction correcting part to achieve said best correction of said eye according to responses of said subject about displayed targets.

2. A device for measuring best corrected visual acuity characteristics as claimed in claim 1, wherein said refraction correcting part is configured to set a value corrected to the minus side by a specified lens refractive index based on corrected visual acuity data of said eye.

3. A device for measuring best corrected visual acuity characteristics as claimed in claim 1, wherein said refraction correcting part is configured to correct at least one of the specified lens refractive index, astigmatism degree and astigmatic axis and to set a value correct to the minus side with respect to the measurement error of said corrected lens refractive index, astigmatism degree or astigmatic axis based on corrected visual acuity data of said eye.

4. A device for measuring best corrected visual acuity characteristics as claimed in claim 1, wherein said adjusting state measuring part comprises:

a light source for measurement located in a position generally corresponding to targets observed by said eye, a diaphragm part provided in a position conjugate with said light source for measurement, and a light receiving optical system having a light receiving part for receiving luminous flux which has passed through said diaphragm part and configured to be conjugate with the anterior segment of said eye.

5. A device for measuring best corrected visual acuity characteristics as claimed in claim 4, wherein said refraction correcting part is configured to set a value corrected to the minus side by a specified lens refractive index based on corrected visual acuity data of said eye.

6. A device for measuring best corrected visual acuity characteristics as claimed in claim 4, wherein said refraction correcting part is configured to correct at least one of the specified lens refractive index, astigmatism degree and astigmatic axis and to set a value correct to the minus side with respect to the measurement error of said corrected lens refractive index, astigmatism degree or astigmatic axis based on corrected visual acuity data of said eye.

7. A device for measuring best corrected visual acuity characteristics as claimed in claim 1, wherein said adjusting state measuring part comprises:

a light source for measurement located to be able to emit luminous flux toward said eye while said eye is observing a target;

a diaphragm part provided in a position conjugate with said light source for measurement, and a light receiving element arranged to receive luminous flux emitted from said light source for measurement and reflected on the anterior segment of said eye which has passed through said diaphragm part and to be conjugate with said anterior segment of said eye, and configured to measure at least one of the size and shape of the opening of the iris in said anterior segment of said eye or at least one of the size and shape of the pupil region of said eye by processing an image of said anterior segment of said eye received by said light receiving element.

8. A device for measuring best corrected visual acuity characteristics as claimed in claim 7, wherein said refraction correcting part is configured to set a value corrected to the minus side by a specified lens refractive index based on corrected visual acuity data of said eye.

9. A device for measuring best corrected visual acuity characteristics as claimed in claim 7, wherein said refraction correcting part is configured to correct at least one of the specified lens refractive index, astigmatism degree and astigmatic axis and to set a value correct to the minus side with respect to the measurement error of said corrected lens refractive index, astigmatism degree or astigmatic axis based on corrected visual acuity data of said eye.

10. A device for measuring best corrected visual acuity characteristics as claimed in claim 1, wherein said adjusting state measuring part comprises:

a light source for measurement located to be able to emit luminous flux toward said eye while said eye is observing a target;

a diaphragm part provided in a position conjugate with said light source for measurement;

a light receiving optical system having a light receiving part for receiving luminous flux which has passed through said diaphragm part, and a polarizing beam splitter for separating luminous flux from said light source for measurement and luminous flux to said diaphragm part, wherein said light receiving part is arranged to receive luminous flux emitted from said light source for measurement and reflected on said anterior segment of said eye and to be conjugate with the anterior segment of said eye.

11. A device for measuring best corrected visual acuity characteristics as claimed in claim 10, wherein said refraction correcting part is configured to set a value corrected to the minus side by a specified lens refractive index based on corrected visual acuity data of said eye.

12. A device for measuring best corrected visual acuity characteristics as claimed in claim 10, wherein said refraction correcting part is configured to correct at least one of the specified lens refractive index, astigmatism degree and astigmatic axis and to set a value correct to the minus side with respect to the measurement error of said corrected lens refractive index, astigmatism degree or astigmatic axis based on corrected visual acuity data of said eye.

13. A method for measuring best corrected visual acuity characteristics comprising:
   a step in which a refraction correcting part corrects the refraction of an eye to be examined of a subject based on corrected visual acuity data of said eye;
   a step of displaying a target to said eye through said refraction correcting part;
   a step in which an adjusting state measuring part measures whether said target is in the adjustable range of said eye;
   a step of correcting a corrective value for said refraction correcting part so that said eye can achieve best correction based on a result of measurement by said adjusting state measuring part, and
   a step of measuring visual acuity characteristics of said eye at a corrective value for said refraction correcting part to achieve said best correction of said eye according to responses of said subject about displayed targets.

14. A device for measuring contrast sensitivity comprising:
   a refraction correcting part for correcting refraction of an eye to be examined of a subject;
   a contrast target display part for displaying contrast targets;
   an adjusting state measuring part for measuring whether a contrast target is in the adjustable range of said eye when said eye looks at said target displayed in said contrast target display part through said refraction correcting part,
   corrective value correcting means for correcting a corrective value for said refraction correcting part so that said eye can achieve best correction based on a result of measurement by said adjusting state measuring part, and
   a contrast sensitivity determining part for determining contrast sensitivity according to responses of said subject about contrast targets displayed through said refraction correcting part corrected by said corrective value correcting means.

15. A device for measuring contrast sensitivity as claimed in claim 14,
   wherein said refraction correcting part is configured to correct at least one of a specified lens refractive index, astigmatism degree and astigmatic axis and to set a value corrected to the minus side with respect to the measurement error of said corrected lens refractive index, astigmatism degree or astigmatic axis based on corrected visual acuity data of said eye.

16. A device for measuring contrast sensitivity as claimed in claim 14,
   wherein said adjusting state measuring part comprises:
   a light source for measurement located in a position generally corresponding to targets observed by said eye;
   a diaphragm part provided in a position conjugate with said light source for measurement, and
   a light receiving optical system having a light receiving part for receiving luminous flux which has passed through said diaphragm part.

17. A device for measuring contrast sensitivity as claimed in claim 16,
   wherein said refraction correcting part is configured to correct at least one of a specified lens refractive index, astigmatism degree and astigmatic axis and to set a value corrected to the minus side with respect to the measurement error of said corrected lens refractive index, astigmatism degree or astigmatic axis based on corrected visual acuity data of said eye.

18. A device for measuring contrast sensitivity as claimed in claim 16,
   wherein said light receiving part is configured to be generally conjugate with the anterior segment of said eye so that the size or shape of the pupil of said eye can be measured using an output of said right receiving part.

19. A device for measuring contrast sensitivity as claimed in claim 18,
   wherein said refraction correcting part is configured to correct at least one of a specified lens refractive index, astigmatism degree and astigmatic axis and to set a value corrected to the minus side with respect to the measurement error of said corrected lens refractive index, astigmatism degree or astigmatic axis based on corrected visual acuity data of said eye.

20. A device for measuring contrast sensitivity as claimed in claim 14,
   wherein said adjusting state measuring part comprises:
   a light source for measurement located to be able to emit luminous flux toward said eye while said eye is observing a target;
   a diaphragm part provided in a position conjugate with said light source for measurement;
   a light receiving optical system for receiving luminous flux which has passed through said diaphragm, and
   a polarizing beam splitter for separating luminous flux from said light source for measurement and luminous flux to said diaphragm, and
   wherein said light receiving part is arranged to receive luminous flux emitted from said light source for measurement and reflected on said anterior segment of said eye and to be conjugate with the anterior segment of said eye.

21. A device for measuring contrast sensitivity as claimed in claim 20,
   wherein said refraction correcting part is configured to correct at least one of a specified lens refractive index, astigmatism degree and astigmatic axis and to set a value corrected to the minus side with respect to the measurement error of said corrected lens refractive index, astigmatism degree or astigmatic axis based on corrected visual acuity data of said eye.

22. A method for measuring contrast sensitivity comprising:
   a step in which a refraction correcting part corrects the refraction of an eye to be examined of a subject based on corrected visual acuity data of said eye;
   a step of displaying a contrast target to said eye through said refraction correcting part;
   a step in which an adjusting state measuring part measured whether said contrast target is in the adjustable range of said eye;
   a step of correcting a corrective value for said refraction correcting part so that said eye can achieve best correction based on a result of measurement by said adjusting state measuring part, and
   a step of measuring contrast sensitivity of said eye at a corrective value for said refraction correcting part to achieve said best correction of said eye according to responses of said subject about displayed contrast targets.

23. A device for displaying contrast sensitivity targets comprising:

a refraction correcting part for correcting refraction of an eye to be examined of a subject;

a contrast target display part for displaying contrast targets;

an adjusting state measuring part for measuring whether a contrast target is in the adjustable range of said eye when said eye looks at a target displayed in said contrast target display part through said refraction correcting part;

a contrast sensitivity determining part for determining contrast sensitivity according to responses of said subject about displayed contrast targets, and corrective value correcting means for correcting a corrective value for said refraction correcting part so that said eye can achieve best correction based on a result of measurement by said adjusting state measuring part, wherein said contrast target display part is configured to display contrast targets to measure contrast when said contrast target is judged to be in said adjustable range of said eye by said adjusting state measuring part.

\* \* \* \* \*